United States Patent [19]

Petrossian et al.

[11] Patent Number: 4,806,484
[45] Date of Patent: Feb. 21, 1989

[54] PERFUSION AIRLIFT BIOREACTOR

[75] Inventors: Ashot Petrossian, San Leandro; Andy DeGiovanni, Berkeley, both of Calif.

[73] Assignee: IGB Products, Ltd., San Leandro, Calif.

[21] Appl. No.: 82,536

[22] Filed: Aug. 7, 1987

[51] Int. Cl.[4] .............................................. C12M 1/12
[52] U.S. Cl. .................................... 435/311; 435/314
[58] Field of Search ............ 261/36 R; 435/311, 286, 435/312, 314, 313, 315; 422/227, 231; 428/903, 902, 357, 398; 210/500.23

[56] References Cited

U.S. PATENT DOCUMENTS

| | | | |
|---|---|---|---|
| 3,186,917 | 6/1965 | Gerhardt et al. | 435/311 |
| 3,418,208 | 12/1968 | Coty | 435/311 |
| 4,545,945 | 10/1985 | Prave et al. | 435/314 |

FOREIGN PATENT DOCUMENTS

| | | | |
|---|---|---|---|
| 112812 | 7/1984 | European Pat. Off. | 435/311 |
| 0148764 | 7/1985 | European Pat. Off. | 435/311 |

*Primary Examiner*—James C. Yeung
*Attorney, Agent, or Firm*—Eugene M. Bond

[57] ABSTRACT

A perfusion airlift bioreactor system that consists of the bioreactor, a media reservoir and a molecular weight cutoff (MWCO) filter positioned between the media reservoir and the airlift bioreactor.

1 Claim, 2 Drawing Sheets

PERFUSION AIRLIFT BIOREACTOR

BACKGROUND OF THE INVENTION

The present invention relates to an improved bioreactor apparatus useful for eukaryotic cell culture, where cell density and bioproduct are increased by, using a molecular weight cutoff filter. The apparatus of the present invention utilizes design features which afford optimum agitation of the cells with minimum mechanical shear force. This is accomplished by utilizing a gas feed to provide gentle aeration and mixing. The novel feature of the invention is the use of an external molecular weight cutoff (MWCO) filter to perfuse nutrients in and waste products out of the bioreactor while maintaining cells and their products within the bioreactor.

SUMMARY OF THE INVENTION

Accordingly, it is an object of the present invention to provide an airlift bioreactor capable of increasing both cell density and bioproduct/s concentration in the airlift bioreactor.

In keeping with this object and the others which will become apparent hereinafter one feature of the airlift bioreactor system is the use of an external molecular weight cutoff filter to perfuse nutrients in and waste products out of the bioreactor while maintaining cells and cell products within the bioreactor. This external cross flow filter is attached to both the bioreactor (the lumen side of the filter) and the media reservoir (shell space of the filter). When culture supernatant and reservoir media are both pumped through the filter, waste products diffuse from the culture and nutrients diffuse into the culture. This allows the cells to achieve a significantly higher density and attendant accumulation of products in this culture supernatant. The increases in cell density and bioproduct/s productivity are proportional to the ratio of the volume of the medium in the reservoir to that of the bioreactor.

DESCRIPTION OF THE PREFERRED EMBODIMENTS

Figure 1:
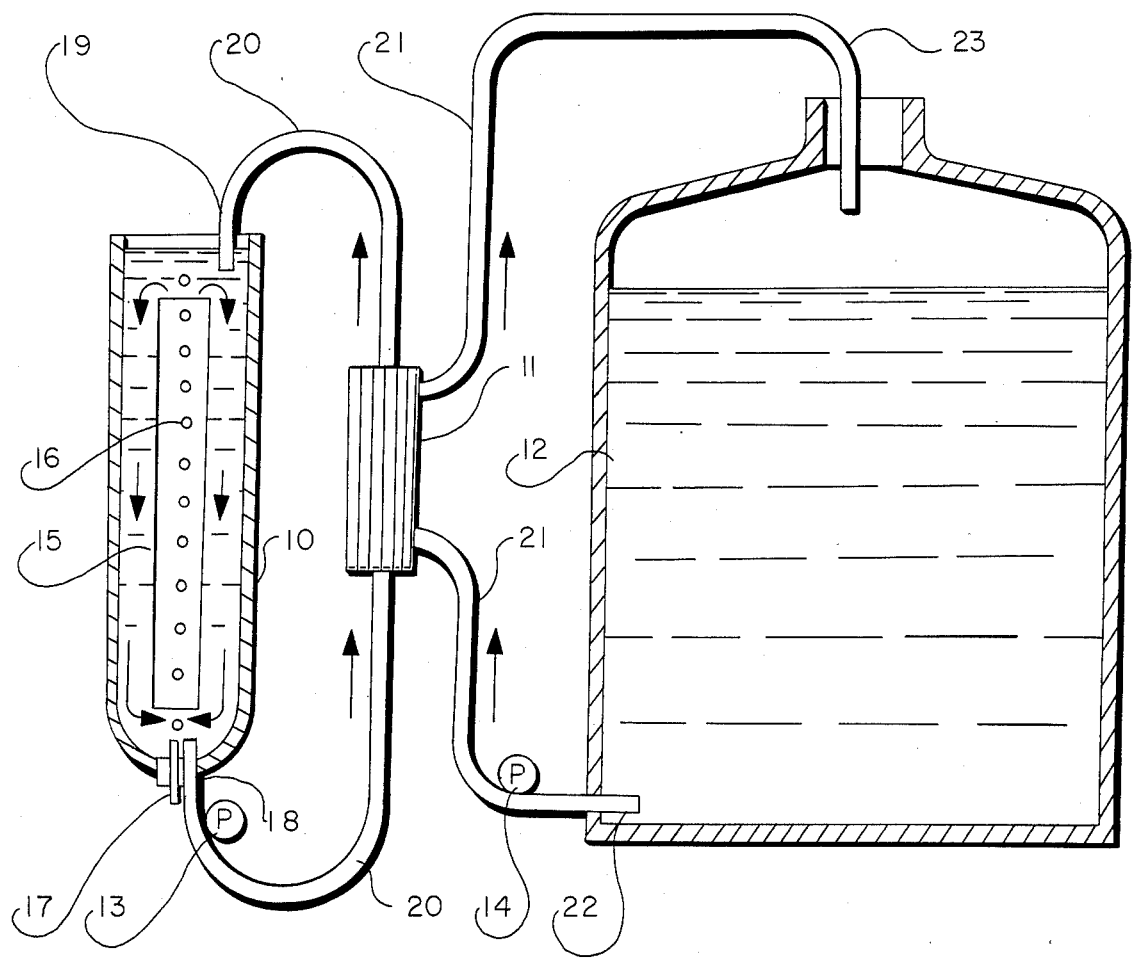
FIG. 1 is a cross-sectional view showing a vertical cross section of the apparatus.

An arrangement for growing micro-organisms is shown in FIG. 1 with the airlift bioreactor (10) of the molecular weight cutoff filter (11) a media reservoir (12) and pumps (13) and (14) which perfuse the media throught the molecular weight cutoff filter. The airlift bioreactor is a vessel having a volume of about 2 liters that includes a cylindrical draft tube (15). An inlet tube (17) is connected to a suitable pump and filter (not shown) for supplying gases (16) for stirring and oxygenation to the medium contained therein. The pump (13) circulates the medium in the bioreactor through the tube (20) and into and out of the bioreactor through apertures (18) and (19). The pump (14) circulates the medium from the storage vessel (12) through the tubes (21) and into and out of the vessel through the apertures (22) and (23).

The invention is illustrated by the following example which illustrates the advantages of the present invention.

Hybridomas were grown in a series 500 2 liter airlift bioreactor furnished by LH Fermentation (a division of Porton International, Inc.) of Hayward, Calif. The operational volume of airlift bioreactor was about 2.3 liters. For comparison, conventional tissue culture was performed in a T-75 flask in a humidified carbon dioxide incubator.

The bioreactor was sparged with a mixture of carbon dioxide, oxygen and air at a rate of about 20 ml per minute. The pH was maintained at $7.0 \pm 0.1$, the temperature at $37 \pm 1°$ C. and oxygen was maintained at air saturation. Hybridoma and medium from the airlift bioreactor and fresh medium from the 50 liter reservoir were perfused through a 19 square foot 30,000 molecular weight cutoff (MWCO) hollow fiber bundle. The cells were grown in a growth medium RPMI-1640 supplemented with 5% fetal bovine serum furnished by J.R. Scientific (a division of Porton International, Inc.) of Woodland, Calif.

The perfusion system incorporating a 2 liter airlift bioreactor and a 50 liter reservoir shown in FIG. 1 resulted in a 15 fold increase in cell density with excellent viability and a 21 fold increase in monoclonal antibody (MAb) concentration in the airlift bioreactor when compared with conventional batch culture using a T-75 flask. The data collected is set out in Table 1 below:

TABLE 1

| BIOREACTOR | MAXIMUM CELL DENSITY ($\times 10^6$ live cells/ml) | MONOCLONAL ANTIBODY CONCENTRATION (micrograms/ml) |
|---|---|---|
| T-75 flask | 0.55 | 5.6 |
| Perfusion airlift bioreactor | 8.10 | 115.0 |

Figure 2:
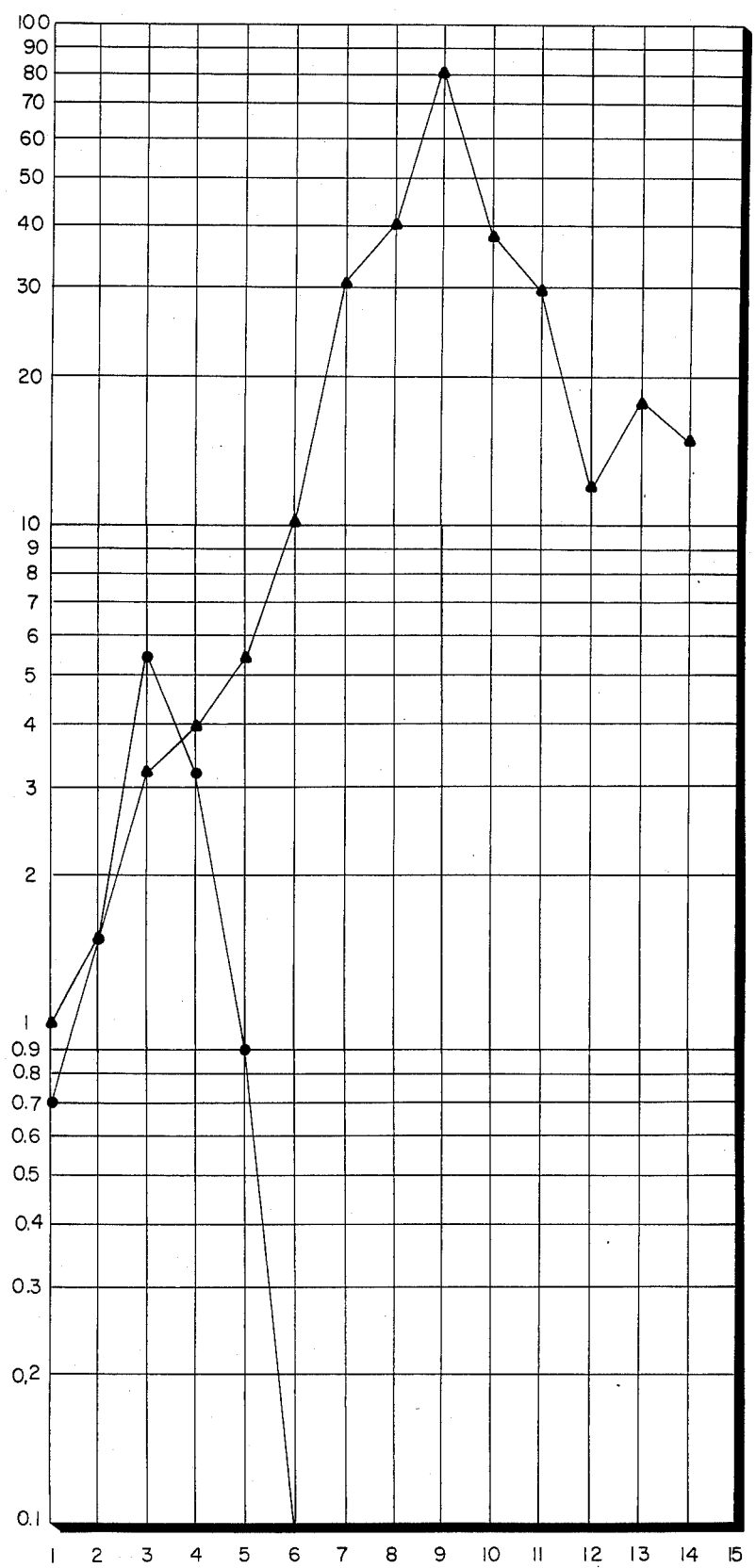
FIG. 2 is a graph showing improved cell density when compared to a T-75 flask.

The data is shown graphically in FIG. 2. The lines with the points drawn as triangles shows hybridoma density when the 2 liter airlift and 50 liter reservoir perfusion system was used with a 19 square foot 30,000 MWCO hollow fiber bundle. The perfusion took place at an average of 40 ml per minute of bioreactor and reservoir medium through the filter. The MAb concentration in micrograms per ml was 115 as set out in the Table above.

The line with the points drawn as circles shows conventional batch growth curve in a T-75 flask with MAb productivity of only 5.6 micrograms per ml.

It is apparent from the data that there is a 21 fold increase in MAb concentration in the airlift bioreactor when compared to a conventional T-75 flask batch culture.

The increased concentration of MAb in a bioreactor renders purification simpler. The ratio of MAB to non-MAb proteins is increased from 0.28 to 6% in the perfusion airlift bioreactor for this low MAb producing hybridoma. The total antibody productivity for a 2 liter airlift perfusion culture is equal to that of a 50 liter airlift bioreactor operated in a batch mode.

Without further analysis the foregoing will fully reveal the gist of the present invention so that others can be applying current knowledge can readily adapt it for various applications without omitting features that from the standpoint of prior art clearly constitute essential characteristics of the generic or specific aspects of this invention.

What is claimed is:

1. An apparatus for growing eukaryotic cells consisting essentially of:
   (a) a two liter airlift bioreactor accomadating eukaryotic cells in suspension, encapsulated or on microcarriers in a medium supporting cell growth,
   (b) a 19 square foot 30,000 molecular weight cutoff hollow fiber bundle filter, positioned between said bioreactor and said media reservoir,
   (c) pump means operably connected to said bioreactor and said filter for circulating said medium into the filter and returning said medium to the bioreactor,
   (d) pump means operably connected to said filter and a 50 liter medium reservoir for circulating said medium from said reservoir to said filter and returning said medium to said medium reservoir,
   (e) pump means operably connected to said bioreactor for admitting air into said airlift bioreactor for stirring the suspension of cells and medium whereby,
   (f) the spent bioreactor medium containing product/s is dialyzed aganst a fresh reservoir medium through said hollow fiber filter.